United States Patent
Brownscombe et al.

(10) Patent No.: US 6,479,699 B2
(45) Date of Patent: *Nov. 12, 2002

(54) PROCESS FOR CARBOXYLATION OF NAPHTHOIC ACID TO NAPHTHALENE DICARBOXYLIC ACID

(75) Inventors: Thomas Fairchild Brownscombe, Houston, TX (US); Donn Anthony DuBois, Houston, TX (US); Susan Secor Pfrehm, Houston, TX (US); William Larry King, Stafford, TX (US)

(73) Assignee: Mossi & Ghisolfi Overseas S.A. (LU)

( * ) Notice: Subject to any disclaimer, the term of this patent is extended or adjusted under 35 U.S.C. 154(b) by 0 days.

This patent is subject to a terminal disclaimer.

(21) Appl. No.: 09/898,890

(22) Filed: Jul. 3, 2001

(65) Prior Publication Data

US 2002/0002302 A1 Jan. 3, 2002

Related U.S. Application Data

(63) Continuation of application No. 09/643,353, filed on Aug. 22, 2000, now Pat. No. 6,441,224
(60) Provisional application No. 60/151,577, filed on Aug. 30, 1999, provisional application No. 60/151,607, filed on Aug. 30, 1999, provisional application No. 60/151,498, filed on Aug. 30, 1999, provisional application No. 60/151,602, filed on Aug. 30, 1999, provisional application No. 60/151,603, filed on Aug. 30, 1999, provisional application No. 60/151,529, filed on Aug. 30, 1999, provisional application No. 60/151,489, filed on Aug. 30, 1999, provisional application No. 60/151,606, filed on Aug. 30, 1999, provisional application No. 60/151,589, filed on Aug. 30, 1999, provisional application No. 60/151,497, filed on Aug. 30, 1999, provisional application No. 60/151,590, filed on Aug. 30, 1999, and provisional application No. 60/151,578, filed on Aug. 30, 1999.

(51) Int. Cl.$^7$ ............... C07C 51/347; C07C 35/08; C07C 63/14; C07C 63/307; C07C 63/313
(52) U.S. Cl. ............... 562/481; 562/482; 562/488
(58) Field of Search ............... 562/481, 482, 562/423, 488

(56) References Cited

U.S. PATENT DOCUMENTS 2,823,231 A * 2/1958 Raecke et al. ............ 260/515
3,487,106 A * 12/1969 Patton et al. ............ 260/515

* cited by examiner

Primary Examiner—Richard L. Raymond
Assistant Examiner—Zachary C. Tucker
(74) Attorney, Agent, or Firm—Renner, Kenner, Greive, Bobak, Taylor & Weber

(57) ABSTRACT

Disclosed is a method for selective carboxylation of naphthoic acid, or other aromatic mono-acids to form primarily 2,3-naphthalene dicarboxylic acid (2,3-NDA) or other aromatic diacids which comprises reacting said aromatic mono-acid in the presence of one or more metal oxide catalysts, alone, or in combination, and in the presence of about 0.2 to 0.8 moles excess of base over aromatic mono-acid, at a temperature of about 380° C. to about 420° C., and, in a second step, disproportionating the product of said selective carboxylation at a temperature above about 420° C. to form a product with a greatly improved yield of 2,6-naphthalene dicarboxylic acid, or other aromatic dicarboxylic acid.

17 Claims, No Drawings

PROCESS FOR CARBOXYLATION OF NAPHTHOIC ACID TO NAPHTHALENE DICARBOXYLIC ACID

CROSS REFERENCE

This is a continuation of application Ser. No. 09/643,353 filed Aug. 22, 2000, now U.S. Pat. No. 6,441,224, the entire disclosure of which is hereby incorporated by reference.

This application is related to U. S. application Ser. Nos. 60/151,577, 60/151,607, 60/151,498, 60/151,602, 60/151,603, 60/151,529, 60/151,489, 60/151,606, 60/151,589, 60/151,497, 60/151,590, and 60/151,578, filed Aug. 30, 1999.

FIELD OF INVENTION

This invention is related to the production of aromatic dicarboxylic acids. More particularly this invention is related to a process for selectively carboxylating an aromatic mono- acid to form primarily an aromatic diacid. One embodiment of the invention is the selective carboxylation of naphthoic acid to form primarily 2,3-naphthalene dicarboxylic acid (2,3-NDA). A second part of the invention is the incorporation of the selective carboxylation into a two-stage process for producing greatly increased yields of aromatic diacid. The invention makes greater use of aromatic rings and obtains a surprisingly high yield of an aromatic dicarboxylic acid, such as, for example, 2,6-naphthalene dicarboxylic acid (2,6-ND4).

BACKGROUND OF THE INVENTION

Aromatic dicarboxylic acids are highly useful organic compounds. They are often used as monomers for the preparation of polymeric materials. For example, terephthalic acid is used to prepare polyethylene terephthalate, a widely used polyester material and the naphthalene dicarboxylic acids, i. e. 2,6-naphthalene dicarboxylic acid, is a particularly useful aromatic carboxylic acid because it can be reacted with ethylene glycol to prepare poly(ethylene-2, 6-naphthalate), PEN. Fibers and films manufactured from PEN display improved strength and superior thermal properties compared with other polyester materials such as polyethylene terephthalate. High strength fibers made from PEN can be used to make tire cords, and films made from PEN are advantageously used to manufacture magnetic recording tape and components for electronic applications. It is desirable to use as pure as possible forms of these dicarboxylic acids in the various applications. It is also desirable to obtain as high a yield as possible of the aromatic dicarboxylic acids.

It is known in the art to prepare aromatic dicarboxylic acids by primarily two methods. One is the liquid phase, metal catalyzed oxidation of an alkyl or acyl substituted aromatic compound. This method is described, for example, in U.S. Pat. Nos. 2,833,816; 3,856,855; 3,870,7544; 4,933, 491; and 4,950,786. This method has drawbacks. The primary disadvantage of the method that involves direct oxidation to 2,6 NDA, is that impurities are trapped in the 2,6 NDA oxidation product which forms upon oxidation as a solid in the oxidation solvent. In order to remove these impurities to a sufficiently low level acceptable for polymerization, the 2,6 NDA product must be purified via multiple steps. These steps typically involve esterification, so that the resulting end product is 2,6-naphthalene dicarboxylate, an ester, rather than the preferred 2,6 naphthalene dicarboxylic acid.

Alternatively, naphthalene monocarboxylic acid and naphthalene dicarboxylic acids other than 2,6-naphthalene dicarboxylic acid can be converted to 2,6-NDA using a disproportionation reaction in the case of the monocarboxylic acids or a rearrangement reaction in the case of other naphthalene dicarboxylic acids. Henkel and Cie first patented a reaction of naphthoic acid salts to 2,6 NDA in the late 1950s. (See U.S. Pat. No. 2,823,231 and U.S. Pat. No. 2,849,482). In these references, it can be observed that excess base was neutralized out of the feed with HCl with the objective of having precisely a 1:1 ratio of K:carboyl. These references demonstrate the disproportionation of benzene to terephthalic acid+benzene. Isomerization of a diacid such as phthalic to terephthalic was demonstrated, as well. It can be observed that the best yield of diacid in this work was about 65%.

It is known in the art that in normal Henkel disproportionation reactions, a significant yield loss occurs during the reaction. This loss, even in the best of circumstances, is usually 3% or more of the weight of the naphthalene dicarboxylic acids (NDAs) theoretically expected to be produced. This loss arises from a mixture of cause, such as coupling of aromatic radicals to form binaphthyls and higher condensed species, decarboxylation of naphthoic acids to naphthalene, and other undesired reactions.

In the absence of charging other carboxylic acid salts (e.g. tricarboxylic benzene acids, or potassium formates, and the like) there is no precedent for obtaining a yield of NDA which exceeds the theoretical yield given by the equation for the Henkel II reaction: 2(potassium naphthoate)→+1 naphthalene+1 naphthalene dicarboxylic acid, where the naphthalene dicarboxylic acid is a mixture of isomers, usually mostly 2,6-naphthalene dicarboxylic acid.

A perplexing question has been how one could more fully use all of the rings present in a feed of aromatic monoacids without the need for alkylation or subsequent oxidation. For example, there has not been a method available in the art to fully use all of the naphthalene rings present in a feed of naphthoic acid.

There does not appear to be any work in the art relating to the possibility of selective carboxylation of monoacids to aromatic diacids using inorganic salts. One Japanese reference claims carboxylation in the presence of oxalates, another organic salt, however only very low molar conversion was demonstrated, with only about 2% of the carboxyl groups present in the oxalate being transferred. (cite unavailable)

There is a great demand for dicarboxylic acids in the production of polymers, yet it has been difficult to produce dicarboxylic acids of good purity and in high yields. It would be a great advance in the art if it were possible to significantly increase the yield of dicarboxylic acids in a disproportionation/isomerization type reaction.

If there were a method available for direct carboxylation of an aromatic monoacid it would provide a significant advance in the art. It would be particularly valuable if there were a method for producing the much sought after 2,6-napthalene dicarboxylic acid in significantly greater yields by direct carboxylation of a feed which is simple to purify and oxidize, such as naptholic acid.

SUMMARY

In the present invention it has been discovered that by operating in an unusual regime of high base and lower temperature, it is possible to produce a significantly higher ratio of NDA to naphthalene than the theoretical ratio of 1.0

In accordance with the foregoing, the present invention comprises a method of directly carboxylating an aromatic monoacid to an aromatic diacid, which comprises:

Reacting said aromatic monoacid with excess base in the presence of a catalyst comprising a metal oxide, particularly an oxide of Group IIB, at a temperature of from, about 350° to 500°.

A second embodiment of the present invention also comprises substantially increasing the yield per pass in a disproportionation/isomerization reaction by a two-stage process comprising:

Heating overbased naphthoic acid salt at a temperature up to about 420° C. for a relatively short period of time to form 2,3-NDA by carboxylation, followed by a heating the product for a relatively longer period of time at a higher temperature, say above 420° C., to isomerize the mainly 2,3-NDA product of the first step to 2,6-NDA.

The invention demonstrates an increase in yield per pass in the disproportionation reaction to form naphthalene dicarboxylic acid, as well as increased throughput, and the reduced recycling of naphthalene. The present invention more fully utilizes all of the naphthalene rings present in a naphthoic acid feed to form naphthalene dicarboxylic acid, without the need for alkylation or subsequent oxidations. The examples demonstrate the direct carboxylation of 2-naphthoic acid, and mixtures of 1- and 2-naphthoic.

The present invention makes it possible to have a low capital, highly efficient disproportionation/isomerization type process to produce naphthalene dicarboxylic acid from naphthoic acid without the need for recycle of naphthalene for alkylation to naphthoic acid. The present invention could greatly simplify and make more productive any process for producing aromatic dicarboxylic acids, especially those that utilize a disproportionation/isomerization reaction.

DETAILED DESCRIPTION OF THE INVENTION

Disproportionation reactions, such as the Henkel reaction, which are known in the art, to produce aromatic dicarboxylic acids, particularly naphthalene dicarboxylic acid, can be represented by the following:

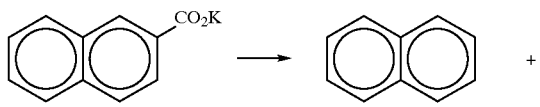

-continued

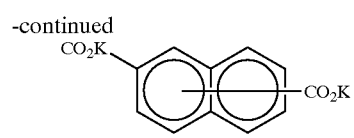

In this reaction, the ratio of base to acid is 1:1. In fact, in early work, HCl was employed in the reaction to neutralize all excess base out of the feed. The best yield of 2,6-NDA demonstrated in early work was about 65%.

In copending U.S. application Ser. No. 60/151,577 incorporated by reference herein in the entirety, the yield of 2,6-NDA in an integrated process incorporating a disproportionation reaction has been optimized to only about a 3% yield loss.

Carboxylation

The present invention comprises the discovery of a method to selectively carboxylate naphthoic acid, or other aromatic mono-acids, to form primarily 2,3-naphthalene dicarboxylic acid (2,3-NDA) or other aromatic diacids. This reaction can be represented by:

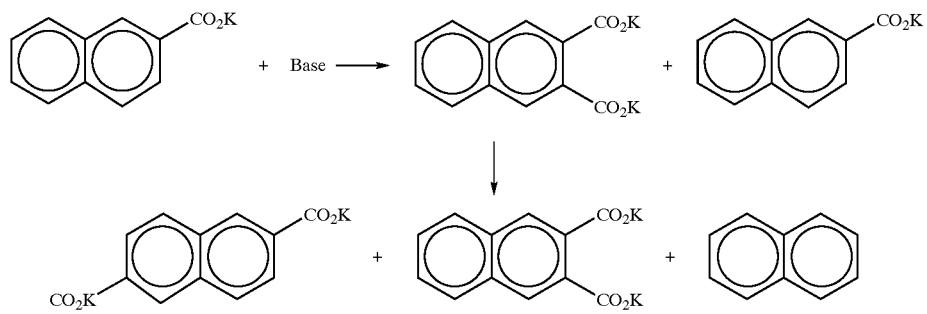

The process includes the use of an excess of basic carbonates, a specific temperature range, and salt feeds of particular X-ray diffraction characteristics. In addition, thermogravimetric analysis (TGA) studies of the feeds suitable for the present invention will reveal a relatively low onset temperature of non-drying weight loss on heating (see Table 2). Differential Scanning Calorimetry(DSC) studies also show such feeds to exhibit a low melting transition (50° C. or more below the normal potassium naphthoate, KNA, melting point of 410° C.) associated with a separate phase.

It is not certain, but it is thought the reaction of the present invention proceeds via the formation of a salt bond between the aromatic monoacid salt and a molecule of bicarbonate or carbonate salt, with the subsequent formation of an aromatic diacid disalt with the COO(−)M(+), (where M is the metal counter ion), groups adjacent to each other on the aromatic ring (e.g., phthalic acid from benzoic acid, 2,3-NDA from 2-NA, 3,4-BDA from 4-carboxy biphenyl, etc.), and a molecule of water and carbon dioxide (from bicarbonate) or of bicarbonate(from carbonate) containing the hydrogen atom removed from the aromatic ring.

Successful practice of the process of this invention requires sufficient mobility to allow the intermolecular carboxyl transfer to occur via the salt bridge, and sufficient stability to avoid decarboxylation. Each system requires, therefore, a specific temperature and pressure range to be effective. However, the key element of the invention is the use of excess carbonate, bicarbonate, or related base, which furnishes, ultimately from carbon dioxide gas, the carboxyl groups to be transferred to the ring.

The starting material for the present invention is an aromatic monoacid. Suitable examples include, but are not limited to benzoic, 1-naphthoic, and 2-naphthoic. Alkyl substituted aromatic monoacids will work.

The excess base is a critical element of the present invention. The optimum level of overbasing is between 0.1 and 1 moles of excess base per mole of acid, although this is probably a function of the exact formulation and conditions used. Using potassium carbonate or bicarbonate and naphthoic acid, a suitable range of overbasing is 1.05–1.8:1, moles potassium to moles of acid. Good results were obtained using 1.2–1.6:1 moles of K per mole of acid.

Suitable bases include alkali metal carbonates. Bases used to provide the excess include, but are not limited to, $K_2CO_3$, $KHCO_3$, $Rb_2CO_3$, $RbHCO_3$, $Cs_2CO_3$, $CsHCO_3$, and other strongly basic carbonates or bicarbonates. The preferred base was potassium carbonate or potassium bicarbonate.

A suitable catalyst for the carboxylation is an oxide of a metal. This can include a number of metal oxides, but is preferably an oxide of a metal selected from IB, IIB, or IIIA of the Periodic Table, including, but not limited to zinc, cadmium, copper, indium, aluminum, and silver. Good results in the carboxylation of naphthoic acid were obtained using zinc oxide.

The temperature for carboxylation in the first embodiment of the present invention will be in a narrow range. Generally it will be about 50° C. below a suitable temperature for disproportionation/isomerization of the starting material. The onset of carboxylation for naphthoic acid, for example, is typically about 380° C., but may be observed in the range between about 375–385° or 390° C. As the temperature is increased, carboxylation takes place up to about 415–425° C., typically about 420° C. Above that temperature potassium salts isomerize and disproportionation begins to predominate.

Two-Stage Process

The second part of the invention, comprising a two-stage conversion to an aromatic diacid, such as 2,6-naphthalene dicarboxylic acid, consists of 1.2 to 2.4:1 potassium: naphthoic acid overbased material, processed through a low temperature stage (3800–425° C.) to make 2,3-NDA, followed by a high temperature stage (ca.435°–455° C.) to convert the 2,3-NDA to 2,6-NDA. The practical overbasing salts will be $KHCO_3$ and $K_2CO_3$, and the exact temperature profile and conditions are critical. More base may be required, depending on the efficiency of utilization of the base in high conversion experiments.

This two-stage process can be effected, inter alia, by feeding overbased naphthoic acid salt through a heated screw device into a reactor of a higher temperature for a longer residence time, by feeding a slurry of such naphthoic acid salt into a small vessel or pipeline followed by a larger vessel at a higher temperature, passing hoppers of salt through first a lower and then a higher temperature zone, or other means which will be obvious to those skilled in the art to effect the two stage reaction process.

In the two-stage process it is helpful to form a slurry of the feed materials. Aromatic hydrocarbons are desired as liquid slurrying media. The slurrying media can suitably be any compound with sufficient thermal stability. It is not restricted to aromatic compounds, however aromatic compounds are suitable. Examples of suitable solvents include a single compound or mixture of compounds selected from a variety of aprotic polycyclic aromatic compounds, such as, for example, naphthalene, methylnaphthalene, dimethylnaphthalene, diphenyl ether, dinaphththyl ether, terphenyl, anthracene, phenanethrene, and mixtures thereof. The preferred medium is naphthalene.

It is demonstrated in the first stage that carboxylation proceeds up to 87% on converted naphthoic acid salt under the specified low temperature reaction conditions. (See Table 1, Ex. 5) In the second stage it is demonstrated that the 2,3-NDA and other isomers so formed may, by raising the temperature, be converted in at least 80% per pass and 98% overall yield to 2,6-NDA, giving an overall field of ca. 20% per pass and about 95% overall to 2,6-NDA from naphthoic acid via the two step process of this invention. Higher conversions in the first step will increase the per pass yield of 2,6-NDA to ca. 70%, in excess of any values disclosed in the literature for a single step conversion of 2,3-NDA to 2,6-NDA, and more than 40% more than the theoretical yield of 2,6-NDA by disproportionation.

So far, 110% vs typical 97% disproportionation yields at 1.2:1 overbasing corresponds to about 65% net utilization of the excess base in bicarbonate vs. KOH systems.

The following examples will serve to illustrate specific embodiments of the invention disclosed herein. These examples are intended only as a means of illustration and should not be construed as limiting the scope of the invention in any way. Those skilled in the art will recognize many variations that may be made without departing from the spirit of the disclosed invention.

EXPERIMENTAL

The examples will demonstrate that by operating in an unusual regime of high base and low temperature, it is possible to produce a significantly higher ratio of NDA to naphthalene (NDA/N) than the theoretical ratio of 1.000. Without these conditions, the best practical result is about 0.97 NDA per Naphthalene (0.97=NDA/N) for the converted K-2-NA salt. With these conditions, NDA/N ratios of greater than 1.5 may be obtained. The inventive process consists of using an excess of base, particularly an excess of the carbonate and bicarbonate salts formed by $CO_2$ precipitation of 2,6 NDA in the acid form, and holding at lower temperatures than the conventional Henkel disproportionation (Henkel II) temperatures, most preferably from about 390° C. to about 420° C. Additionally, the most preferred embodiment involves preparation of a finely dispersed mixture of the excess base salts with the naphthoic acid salts, often indicated by low melting peaks in the DSC (differential scanning calorimetry) scans of the feed salts. Further, the reaction may be accelerated by addition of small amounts of larger alkali cation salts (e.g., Cs) which also seem to depress the melting point and improve the mixing of the carbonic and naphthoic salts. In the examples zinc salts were used to promote the reaction although other salts may be used, as is known in the literature (Cd, etc.). The zinc salts, preferred for cost and low toxicity, may be used as the oxide, carbonate, or other inorganic salt, or the organic salt of the naphthoic acid feed, conveniently formed by reaction of the naphthoic acid with zinc oxide under elevated temperature.

The experimental procedure comprises adding together naphthoic acid, water, and excess bicarbonate, mixing these starting materials, and heating to form potassium naphthoate, mixed with excess carbonate and bicarbonate. Alternatively, the naphthoic acid is ground up and added to an aqueous solution of $K_2CO_3$ to form a salt that is soluble in base. The mixture is heated to about 100° C. for about 10 to 30 minutes. Those skilled in the art would realize that one could heat at a higher temperature by adding pressure to the water; and one could use a lower temperature if a longer reaction time is used. Typically, the mixture was reacted at about 100° C. for about 20 minutes. In addition, particle size and rate of addition would be affected by the ratio of base to naphthoic acid. The naphthoic acid is dissolved in base and the water with solids is stripped.

The best results have been obtained with a formulation prepared from naphthoic acid, an excess of potassium bicarbonate, a specific drying regimen such that the starting materials exhibit specific x-ray diffraction characteristics, and thermogravimetric analysis characteristics characterized by a relatively low onset temperature of non-drying weight loss on heating (see Table 2). The drying regimen involves heating the solids at about 175° C. for about 2 hours under 0.8 torr mm Hg pressure. Especially preferred feeds are ones that have mixtures of the following "two theta" peaks (among others) in the powder X-ray diffraction patterns of the initial (gently dried, air exposed) feed salt mixture: 14.0, 28.5, 38.2, 13.6, 27.3, 32.0, and 36.7 degrees two theta. Not all the peaks need be there in all samples, but in general feeds which have these peaks (as well as others) will give good yields. These peaks correspond to lattice spacings of 6.32, 3.13, 2.35, 6.52, 3.26, 2.80, and 2.45 Angstroms in Bragg d spacing.

Further description of the experimental procedure includes alternative ways of mixing the starting materials before the drying regimen:

1. The powdered acid can be added to the aqueous material.
2. The acid can be dissolved in hydrocarbon solvent at elevated temperature where water with base and catalyst are added and allowed to react as the water is boiled out of the mixture.
3. The acid and base can be contacted with each other at an elevated temperature in the range of about 90–110° C.
4. The water phase or aqueous salts can be dripped into the hydrocarbon solvent.
5. Powdered naphthoic acid can be dripped into a solution of aqueous base with catalyst suspended.

In some examples a eutectic mixture was employed. A eutectic mixture provides the lowest melting point of a mixture of two or more alkali metals that is obtainable by varying the percentage of the components. Eutectic mixtures have a definite minimum melting point compared with other combinations of the same metals. For example, though the melting point of $LiCO_3$ is 622° C., in a eutectic mixture of alkali carbonates the melting point can be 400° C. What is required in the present examples, where a eutectic mixture is employed, is the right mixture of alkali metal carbonates where the melting point is less than about 400–420° C. Generally the ratio of alkali metal carbonates in the eutectic mixture is about 1:1:1, but it can vary. One eutectic mixture used as a solvent was $K_2CO_3$, $Rb_2CO3$, $Cs_2CO_3$, and optionally including $Na_2CO_3$.

Best results have been obtained with ZnO as the catalyst for carboxylation, although a variety of metal oxides will work as catalysts.

Optimum temperatures for the carboxylation reaction are typically about 50° C. below the optimum for a disproportionation/isomerization reaction as known in the art for similar composition.

Though potassium bicarbonate works well, any "overbased" potassium, rubidium, or cesium carbonate salt, preferably between 1.2:1 alkali metal:naphthoic acid mole ratio and 2.0:1 alkali metal to naphthoic acid ratio appears to make the reaction possible, if run carefully at the optimum temperature and conditions for the specific material. A preferred range of overbasing is between 1.2–1.6:1, although this is probably a function of the exact formulation and conditions used. More than half of the excess base present may be transferred to the rings as carboxyl groups. To fully convert the NA to 2,3-NDA, a full mole of excess base is required. In copending U.S. patent application Ser. No. 60/151,606, filed of even date and incorporated by reference herein in its entirety, it was shown that overbasing of 0.01 to 0 20 moles per mole of monoacid in disproportionation gives optimum 2,6-NDA yield under normal condition; and that application also showed excellent yields (>95%) of isomerization of the diacid disalts (including K2-2,3-NDA) in the presence of 0.1 to 0.2 moles of excess base.

Though the art would indicate water should be avoided in a reaction of this type, it has been found in the present invention that a small amount of water, say less than 1000 ppm, seems to actually facilitate the reaction.

It is speculated the beneficial effects are due to the effect of the water of introducing increased mobility into the salts, specifically allowing the salt complexes more rotational freedom and also by stabilizing the charged species formed as intermediates. It is also possible a small amount of water stabilizes the original finely divided mixed crystalline low melting materials that make the best feeds. However, a significant amount of water, say, for example in excess of ca. 700–1000 ppm, interferes with the reaction by beginning to favor the decomposition of the salts (decarboxylation). A significant amount of water, 0.2% or more, becomes damaging by promoting yield loss.

In the second embodiment of the present invention, the two-stage process consists of 1.2 to 2.4:1 K:NA overbased material, processed through a low temperature stage (380°–425° C.) to make 2,3-NDA, followed by a high temperature stage (ca.435°–455° C.) to convert the 2,3-NDA to 2,6-NDA. The practical overbasing salts will be $KHCO_3$ and $K_2CO_3$, and the exact temperature profile and conditions will be critical. More base may be required, depending on the efficiency of utilization of the base in high conversion experiments. So far, 110% vs typical 97% disproportionation yields at 1.2:1 overbasing corresponds to about 65% net utilization of the excess base in bicarbonate vs. KOH systems. If this efficiency is the limit, 2.0:1 overbasing would yield 165% of disproportionation and 180%(90% direct yield of NA to 2,6-NDA) would require ca. 2.3:1 overbasing in the above proposed range.)

Using the two-stage process of this invention, comprising carboxylation of naphthoic acid and subsequent disproportionation and isomerization to 2,6-NDA at high conversion per pass of 80% or more, yields of up to 110% of the theoretical yield for a "Henkel" disproportionation have been observed at conversions of naphthoic acid up to 90%. At lower conversions, higher excesses of naphthalene dicarboxylic acid have been observed, up to ca. 76% of the converted naphthoic acid.

EXAMPLES 1–6

Examples 1–6 demonstrate the first stage, comprising the selective carboxylation of naphthoic acid to 2,3-naphthalene dicarboxylate. Examples 1–6 were carried out using ZnO catalyst and K2NA prepared by 1.0 2NA+1.2 $KHCO_3$. Runs were carried out in a fluidized sand bath using reactor vessels constructed from ⅜" diameter stainless steel tubing. The reactors were charged with 250 psi $CO_2$ at room temperature.

Yields were measured by proton NMR. In all the runs only a fraction of the potassium naphthoate (KNA) was converted to diacid (2,3-isomer), however, of the KNA that was consumed, 0.695 of that mass should be diacid. In the cases of direct carboxylation, the consumed KNA is actually producing more than theoretical amounts of diacid.

Example 6, which was carried out at higher temperature shows typical disproportionation/isomerization behavior to give predominantly 2,6-NDA in high selectivity (>60% of NDAs), except that total yield of 2,6-NDA and 2,3-NDA is 110% of theoretical, whereas all lower temperature runs reveal an average K2NA consumption of 25%, little 2,6-isomer, and greater than theoretical disproportionation yield. Also consistent with direct carboxylation are the very low naphthalene yields.

tion reaction as discussed above. The low temperature peak is about 1/10 the size of the high temperature onset peak (typically 1.5–4% vs 20–30% weight loss). The low temperature peak would represent water (from carboxylation, drying occurring at much lower temperature) and the high temperature peak represents naphthalene of disproportionation in the simplest model. Some examples also exhibit an intermediate peak.

In this model, the lower temperature is then taken as the minimum temperature for the carboxylation reaction, and the upper temperature as the upper limit for carboxylation and lower limit for disproportionation. It is desirable to operate As near to the upper limit for carboxylation (higher temp.) as possible to achieve the maximum rate of

TABLE 1

| Example LR23294 | Temp/time ° C./min | Theoretical K2NA in NMR tube (mg) | Actual K2NA Detected (mg) | Actual 2,3 - isomer detected (mg) | Actual 2,6 - isomer detected (mg) | Naphthalene Yield | Diacid yield Based on Consumed K2NA |
|---|---|---|---|---|---|---|---|
| Ex. 1 178-1 | 410/60 | 36.7 | 28.3 | 8.3 | 0.6 | 7% | 152% |
| Ex. 2 178-2 | 410/60 | 39.29 | 28.5 | 9.5 | 1.3 | 13% | 159% |
| Ex. 3 178-3 | 410/30 | 36.06 | 27.8 | 9.0 | 1.1 | 9% | 176% |
| Ex. 4 178-4 | 410/15 | 36.00 | 29.0 | 6.4 | 0.6 | 11% | 144 |
| Ex. 5 191 | 410/60 | 37.66 | 29.8 | 9.5 | 0 | 8% | 174% |
| Ex. 6 192 | 450/60 | 37.01 | 13.2 | 5.6 | 12.7 | 97% | 111% |

It should be noted that Example 5 (run 191) represents a utilization of 78% of the excess base (K) to produce excess carboxylate. If this ratio holds at higher levels if base proposed above, the proposed theoretical formulations would yield ca. 90% yields of 2,6-NDA ultimately from NA, or 180% of the theoretical disproportionation yields. Consisted- with the very high level of carboxylation is the very low level of naphthalene observed (8% of theory). If this level held to high conversion (conversion in –191 was only 21% of KNA salt, due to lack of sufficient excess base), one would expect 92% yield of 2,6-NDA overall (184% of disproportionation yield). Run –192 at 65% conversion gave about 50% utilization of the excess base. Surplus base is recycled to contact fresh acid after the removal of the product naphthalene dicarboxylic acid.

EXAMPLE 7

Example 7 was an experiment designed to show thermogravimetric analysis (TGA) reaction temperature onset as a function of overbasing. The overbasing ratio is the ratio of potassium in the base used to 2-naphthoic acid used to generate the salt. All mixtures contain ca. 17% ZnO.

The onset temperature of reaction by thermogravimetric analysis (TGA) is the temperature at which non-drying weight loss begins for the given system being heated at 10° C./min. under $N_2$ in this example. It is a measure of reactivity of the system, influenced by molecular mobility and carbonate: acid ratio. Naphthalene evolution has been demonstrated for these systems in a pyroprobe connected to a mass spectrometer, although it is possible in some instances the weight loss could begin with water from decomposition of bicarbonate formed from the carboxylacarboxylation, but preferably below it, to avoid consumption of naphthoic acid by disproportionation before it can be carboxylated.

$KHCO_3$ is mostly converted to $K_2CO_3$ during the 175° C. drying (>75%) and is essentially completely converted by 300° C. Results are shown in Table 2:

TABLE 2

| Overbasing Ratio (a) | Base Used | Onset of reaction ° C. Low Temp Peak | Onset of reaction ° C. High Temp Peak |
|---|---|---|---|
| 1.0 | $K_2CO_3$ | 380 | 444 |
| 1.2 | $KHCO_3$ | 365 | 414 |
| 1.2 | $K_2CO_3$ | 250 | 420 |
| 1.4 | $K_2CO_3$ | 240 | 425 |
| 2.0 | $K_2CO_3$ | 260 | 420 |

EXAMPLES 8–19

Examples 8–19 demonstrate isomerization. In examples 8–19 the following abbreviations are used: PA=Phthalic Acid; IPA=Isophthalic Acid; TPA=Terephthalic Acid; PAN= Phthalic Anhydride. Examples 8–19 were run at 430–460° C., 250 psi $CO_2$ pressure prior to heating, 3 hours at temperature, no mixing, 150 cc Hoke vessel as reactor, band heater. Hastelloy C vessel, barricaded, for potentially corrosive mixtures, other in s. s. in lab. Final pressures 400–1100 psig, 600–800 psig typical. Results for the isomerizations of Examples 8–19 are shown in Table 3.

TABLE 3

| Components | | $D_2O$ Sol. Products mg/g | | Feed charged mg/g* | Bulk density (d) g/cc | Rate production G/L/hr | Final/initial Solid wts. | Comments |
|---|---|---|---|---|---|---|---|---|
| Ex. 8 | | PA | 1.6 | 165 | 2.0 | — | 0.871 | 430° C. |
| $K_2PA$ | −5.27 | BA | 54.8 | — | melt | 36 | | |
| $K_2SO_4$ | −4.65 | | | | | | | |
| $Na_2SO_4$ | −4.79 | | | | | | | |
| $ZnSO_4$ | −7.01 | | | | | | | |
| Ex. 9 | | PA | 19.7 | 152 | 1.8 | — | 0.834 | 430° C. |
| $K_2PA$ | −3.02 | BA | 191.4 | — | melt | 115 | | |
| $Li_2CO_3$ | −1.25 | | | | | | | |
| $Na_2CO_3$ | −2.22 | | | | | | | |
| $K_2CO_3$ | −1.96 | | | | | | | |
| $V_2O_5$ | −5.01 | | | | | | | |
| Ex. 10 | | BTA | 0.2 | 500 | 1.45 | 0.1 | 0.6 | 460° C. run |
| | | TPA | 3.6 | | melt | 1.7 | | 300 psig |
| Pan | 5.06 | IPA | 0.8 | | | 0.4 | | autog. |
| H+ Mordenite | 5.12 | PA | 0.6 | | | — | | $CO_2$ |
| | | BA | 7.9 | | | 3.8 | | |
| Ex. 11 | | PhH | 0.3 | 348 | 1.2 | 0.1 | 0.762 | 460° C. run |
| | | TPA | 106 | | powder | 42 | (0.853 | |
| PAn | 4.66 | PA | 4.4 | | average | — | of theory) | |
| $K_2CO_3$ | 4.49 | BA | 30 | | | 12 | | |
| ZnO | 4.25 | | | | | | | |
| Ex. 12 | | TPA | 172 | 337 | 1.2 | 69 | 0.664 | 460° C. |
| | | PA | 7.8 | | powder | — | | |
| PA | 4.66 | BA | 37.4 | | avg. | 15 | | |
| $K_2CO_3$ | 4.49 | | | | | | | |
| $Ag_2O$ | 4.68 | | | | | | | |
| Ex. 13 | | BTA | 25.8 | 332 | 0.7 | 6.0 | 0.777 | 460° C. run |
| | | TPA | 130 | | powder | 60.3 | | |
| PA | 3.12 | IPA | 34.9 | | | 8.1 | | |
| $Cs_2CO_3$ | 6.27 | PA | 6.7 | | | — | | |
| | | BA | 23.6 | | | 5.5 | | |
| Ex. 14 | | BTA | 0.3 | 117 | 2.2 | 0.2 | 0.849 | 460° C. |
| −172 | | TPA | 0.33 | | | melt | 0.24 | |
| Pan | 2.06 | IPA | 0.57 | | | 0.42 | | |
| $Li_2CO_3$ | 2.64 | BA | 1.25 | | | 0.92 | | |
| $Na_2CO_3$ | 3.17 | | | | | | | |
| $K_2CO_3$ | 2.88 | | | | | | | |
| $Cs_2CO_3$ | 5.82 | | | | | | | |
| $Ag_2O$ | 1.0 | | | | | | | |
| Ex. 15 | | BTA | 1.46 | 215 | 1.4 | 0.7 | 0.864 | 460° C. |
| 23157-23 | | TPA | 15.6 | | powder | 7.3 | | diacids 78% |
| K, Rb, Cs, Zn | | IPA | 3.39 | | | 1.6 | | TPA |
| $CO_3$ eutectic | 3.1 | PA | 1.13 | | | — | | |
| $Al_2O_3$ | 15.2 | BA | 13.4 | | | 6.2 | | |
| Pan | 3.03 | | | | | | | |
| Ex. 16 | | BTA | 1.43 | 131 | 1.4 | 0.7 | 0.888 | 460° C. |
| −26 | | TPA | 3.59 | | powder | 1.7 | | BTA, BA |
| K, Rb, Cs, Zn | | IPA | 1.81 | | | 0.8 | | rates |
| $CO_3$ eutectic | 5.03 | PA | 0.81 | | | — | | Up/feed |
| $Al_2O_3$ | 15.2 | BA | 8.68 | | | 4.1 | | TPA down |
| Pan | 3.03 | | | | | | IPA flat | |
| Ex. 17 | | BTA | 0.65 | 114 | 1.5 | 0.3 | 0.895 | 460° C. |
| −33 | | TPA | 7.70 | | powder | 3.9 | | 84% TPA of |
| K, Rb, Cs, Zn | | IPA | 1.15 | | | 0.6 | | diacids |
| $CO_3$ | 8.06 | PA | 0.28 | | | — | | 3 hr run |
| eutectic | | | | | | | | |
| $Al_2O_3$ | 15.57 | BA | 3.27 | | | 1.6 | | |
| Pan | 3.05 | | | | | | | |
| Ex. 18 | | ETA | 0.40 | 114 | 1.5 | N/a | 0.898 | 460° C. |
| −30 | | TPA | 0.65 | | powder | | | 16 hrs |
| dup Ex. 17, | | IPA | 0.92 | | | | | |
| except went | | PA | 0.45 | | | | | |
| 16 hrs | | BA | 2.58 | | | | | |
| Ex. 19 | | BA | 0.78 | 143 | 2.0 | 1.3 | 0.879 | 4600-31 melt |
| −31 | | | | | melt | | | |
| $K_2PA$ | 5.26 | | | | | | | |
| $Cs_2SO_4$ | 7.99 | | | | | | | |
| $K_2SO_4$ | 4.71 | | | | | | | |
| $ZnSO_4$ | 7.07 | | | | | | | |

The analytical procedure was as follows: The entire solid sample was homogenized by grinding, and one gram was digester with 10 cc of $D_2O$ spiked with trimethylsilyl sodium propionate(TSP) for 4 hours at 70° C. One cc of solution was then analyzed by H-nmr, and values of identified species (PA, IPA, TPA, BA, etc.) calculated vs. TSP standard and reported Multiplication of mg observed in sample×10 yields mg/g of original solid from reactor.

If the feed was charged as a solid (e.g. PAN), it was mixed with the other materials as powders and presumed to be uniformly distributed. In such cases the mg/g is simply the fraction by weight of material charged. If the feed charged Us a liquid under the reaction conditions, it was treated as a solid, above.

Estimated bulk density for the mixture under reaction conditions may not be the same as the components at room temperature. It is assumed that the molten salt species have a density of 0.68 of that of the pure solid phases when molten. The diacid salts are assumed not to melt (basis experiments with TPA salts) and are taken at their solid phase densities. If the system is not molten (i.e., recovered as a powder), the phase densities are divided by 3 to get an approximation of the bulk density. The idea is to estimate bulk density under reaction conditions.(g/cc)

Calculated rate of production of specified component is based on the observed production per gram of solid, the bulk density, and the time. (g/liter/hour)

Ratio of weight of material charged to weight recovered, some losses are normal due to adhesion to walls, funnels, scrapers, etc. and quantitative recovery is not expected—but gross discrepancies indicate volatilization, loss of $CO_2$, etc.

Feed per g calculated per unit volume of 1 g of solid.

EXAMPLES 20–25

Examples 20–25 relate specifically to the production of naphthalene dicarboxylic acid (NDA) and further demonstrate that operating in the regime of the present invention of high base and low temperature, it is possible to produce a significantly higher ratio of NDA to Naphthalene (NDA/N) than the theoretical ratio of 1.000. Without these conditions, the best practical result is about 0.97 NDA per Naphthalene (0.97=NDA/N) for the converted K-2-NA salt. With these conditions, NDA/N ratios of greater than 1.5 may be obtained. The inventive process consists of using an excess of base, particularly an excess of the carbonate and bicarbonate salts formed by $CO_2$ precipitation of 2,6 NDA in the acid form, and holding at lower temperatures than the conventional Henkel disproportionation (Henkel II) temperatures, most preferably from about 390° C. to about 420° C. Additionally, the most preferred embodiment involves preparation of a finely dispersed mixture of the excess base salts with the naphthoic acid salts, often indicated by low melting peaks in the DSC (differential scanning calorimetry) scans of the feed salts. Further, the reaction may be accelerated by addition of small amounts of larger alkali cation salts (e.g., Cs) which also seem to depress the melting point and improve the mixing of the carbonic and naphthoic salts. In the examples zinc salts were used to promote the reaction although other salts may be used, as is known in the literature (Cd, etc.). The zinc salts, preferred for cost and low toxicity, may be used as the oxide, carbonate, or other inorganic salt, or the organic salt of the naphthoic acid feed, conveniently formed by reaction of the naphthoic acid with zinc oxide under elevated temperature.

A convenient way of forming the preferred disordered salt mixture is to charge a mixture of the organic naphthoic acid potassium (or mixed alkali) salt in water with dissolved inorganic (carbonate, bicarbonate) salts and suspended zinc oxide, into a vessel of hot oil, preferably naphthalene or another stable hydrocarbon consistent with the process. By this means, the solution is rapidly converted to a porous solid of comparatively fine crystallite size and intimately mixed organic and inorganic salts. In order to analyze precisely for the amount of products produced, three repeated extractions of the salt phase with KOH in $D_2O$ and a suitable protonic internal standard for nmr were made to analyze for the acids by quantitative nuclear magnetic resonance, and the hydrocarbon (naphthalene) portion of the product was analyzed by digesting the sample in d6 DMSO (deuterio dimethyl sulfoxide) with trioxane as the internal protonic standards By using test synthetic salt mixtures of K2-2,3 NDA, K2-2,6 NDA, K-2-NA, and naphthalene, it was shown that the error in the analysis by this method was less than 1% mole of the contained species analyzed.

EXAMPLE 20

Example 20 describes the preparation of feed salt. The feed salt samples heated to induce disproportionation were first prepared as mixed salts by stripping from aqueous solution, including 5% by weight of dried ZnO powder, drying at 125° C. in a vacuum oven, and were then ground in a micromill to produce a fine (5–10 micron) powder. The powder was then dried at 175° C. in a vacuum oven at 1–2 torr pressure. The dry powder at 175° C. was conveyed quickly through the atmosphere and charged into a 100 cc autoclave heated to 130° C. to ensure dryness, sealed, and purged repeatedly with $CO_2$ to remove most of the air and provide the gas cap for the disproportionation reaction. The autoclave was then fitted onto a "rotisserie" rack in a Blue M convection furnace designed to maintain temperature at about +/−2° C. and heated for the required time. Heat up and cool down in this oven require about 15 and 20 minutes respectively. The oven is purged with nitrogen in the event a leak releases potentially flammable naphthalene over the heater in the air circulation pathway.

EXAMPLE 21—COMPARATIVE

In the comparative example, 5.0 g of mixed salts containing 1.00 to 1.1:1 K:2-NA ratio are prepared as described with 0.25 g of ZnO, charged into the autoclaves as described and heated at 450° C. for 1.5 hours. The resulting NDA/N ratio of the product is between 1.00 and 0.95 depending on the exact preparation (amount of carbonate, bicarbonate, crystal size, DSC trace, XRD pattern of product salt, uniformity of mixing, etc.) Conversion of 2-NA to products is from 80% to 99% depending on $CO_2$ pressure and exact conditions as described above. Selectivity to 2,6 NDA in the NDA product is more than 70%.

EXAMPLE 22

In example 22, a ratio of inorganic (carbonate, bicarbonate) basic salts to 2-naphthoic acid of 1.3:1 is used to prepare 5.0 g of mixed salts. The resulting salt is prepared as described with 0.25 g of ZnO, and added as described to the autoclaves and heated for 1.5 hours with a minute hold period at 420° C. and 70 minutes at 450° C. (including transient heating to the higher temperature. The resulting NDA to N ratio is an average of 1.15 in this case, indicating a surplus of up to ca. 20% of NDA. In this example, in average conversion of 2-NA salt of 94% is observed, with an average selectivity to 2,6 NDA of 88% of the total NDAs formed. As usual, the major other NDA salt formed is the 2,3 isomer.

EXAMPLE 23

In Example 23, the mixture of example 22 is heated to 450° C. directly. An NDA/N ratio of 1.03 to 1.14 is observed, indicating that carboxylation of the naphthoic acid may occur during the temperatures of conventional Henkel isomerization and the normal heat-up period, provided sufficient excess base is present.

EXAMPLE 24

In Example 24, a variety of K:2-NA ratios is used, from 1.2:1 to 2.0:1, with the slow heat up cycle of Example 22. The resulting NDA yields based on 2-NA conversion range up to 40% excess of theoretical yield from the disproportionation reaction. 2,3 NDA is the major non-2,6 NDA isomer formed, but again 2,6 NDA is typically about 80–90% of the total NDAs. An optimum appears around 1.3 to 1.6 to 1 K:2-NA ratio, probably due to an optimal level of mixing in the combined organic/inorganic (naphthoate/carbonate&bicarbonate) salts and dispersion of the catalyst. Additionally, it is thought that ratios of 2.0 to 1 or less are preferred strictly on yield grounds due the reduced level of naphthoate per unit volume in the high ratio materials. In addition, it is more difficult to recycle the salts at high ratios, due to reduced effectiveness of the preferred $CO_2$ precipitation of 2,6 NDA at high base levels. Therefore it is apparent that for a given process configuration, there will be an optimum level of excess base, an optimum temperature profile and residence time, etc.

EXAMPLE 25

In Example 25, the experiment of Example 22 is repeated with substitution of 9% of the potassium with Cs. It is observed that the NDA to N ratio is about 1.1:1. However, if the temperature is lowered to 430° C. it is also observed that the kinetics are substantially faster, with a greater rate of production of NDAs at 430° C. than at 450° C. in the pure potassium case. It is thought that the Cs/K mixture favors the disordered salt phase preferred for the carboxylation and disproportionation and isomerization reactions. It is further observed that eutectic mixtures of 1- and 2-napthoic acids as a mixed salt of Cs, K, and Rb may be formed over a fairly wide ratio of alkali ions and organic isomers. Such eutectics may melt as low as about 300° C., and give a rapid disproportionation and isomerization as well as carboxylation as low as 380° C. However, they are not generally the most preferred embodiment, due to the cost of the heavier alkali ions and the difficulties of separation in the $CO_2$ precipitation phase (oiling out of salts etc.).

We claim:

1. A process for selective carboxylation of an aromatic monoacid to an aromatic diacid which comprises: reacting said mono-acid in the presence of excess base, forming a solid salt, drying said salt, and reacting in the presence of a catalyst selected from one or more oxides of a metal, alone or in combination, at a temperature between about 350° C. and 500° C. to form a dicarboxylic acid.

2. The process claim 1 wherein the mono-acid is selected from the group consisting of benzoic acid, 1-naphthoic acid, and 2-naphthoic acid.

3. The process of claim 1 wherein the mono-acid is selected from the group consisting of alkyl substituted compounds of benzoic acid, 1-naphthoic acid, and 2-naphthoic acid.

4. The process of claim 2 wherein the mono-acid is naphthoic acid.

5. The process of claim 1 wherein the base is present in an amount of 0.1 to 1.0 molar excess of base to mono-acid.

6. The process of claim 1 wherein the base is selected from the group consisting of alkali metal carbonates and bicarbonates.

7. The process of claim 6 wherein the base is selected from the group consisting of $K_2CO_3$, $KHCO_3$, $Rb_2CO_3$, $RbHCO_3$, $Cs_2CO_3$, and $CSHCO_3$.

8. The process of claim 7 wherein the base is selected from potassium carbonate and potassium bicarbonate.

9. The process of claim 8 wherein the base is present in excess in a ratio of 1.2–1.8 to 1, potassium to mono-acid.

10. The process of claim 9 wherein the base is present in a ratio of 1.2–1.6 to 1, potassium to mono-acid.

11. The process of claim 1 wherein the temperature for carboxylation is from about 380° C. to about 420° C.

12. The process of claim 1 wherein the catalyst is an oxide of a metal selected from Group IB, IIB, or IIIA of the Periodic Table.

13. The process of claim 12 wherein the metal is selected from the group consisting of oxides of zinc, cadmium, copper, indium, aluminum, and silver.

14. The process of claim 13 wherein the catalyst is zinc oxide.

15. The process of claim 1 further comprising the presence of up to 1000 ppm water in the reaction.

16. The process of claim 1 further comprising disproportionating said product dicarboxylic acid at a temperature above about 420° C. to form additional aromatic diacid.

17. The process of claim 1 wherein said solid salt is dried by heating the solids at about 175° C. for about 2 hours under 0.8 torr mm Hg pressure.

* * * * *